US012667591B2

(12) United States Patent
Schlesinger et al.

(10) Patent No.: US 12,667,591 B2
(45) Date of Patent: Jun. 30, 2026

(54) USE OF PLATELET-BASED PRODUCTS FOR TREATMENT OF CAPSULAR CONTRACTURE PROXIMATE BREAST IMPLANT

(71) Applicant: L & O Medical, LLC, Honolulu, HI (US)

(72) Inventors: Stephen Lawrence Schlesinger, Honolulu, HI (US); Owen Tsan Mo Chan, Honolulu, HI (US)

(73) Assignee: L & O Medical, LLC, Honolulu, HI (US)

( * ) Notice: Subject to any disclaimer, the term of this patent is extended or adjusted under 35 U.S.C. 154(b) by 0 days.

(21) Appl. No.: 19/420,412

(22) Filed: Dec. 15, 2025

(65) Prior Publication Data

US 2026/0102429 A1 Apr. 16, 2026

Related U.S. Application Data

(63) Continuation of application No. 19/048,619, filed on Feb. 7, 2025, now Pat. No. 12,521,417.

(60) Provisional application No. 63/550,913, filed on Feb. 7, 2024.

(51) Int. Cl.
*A61K 35/16* (2015.01)
*A61K 9/00* (2006.01)
*A61P 43/00* (2006.01)

(52) U.S. Cl.
CPC ............ *A61K 35/16* (2013.01); *A61K 9/0019* (2013.01); *A61P 43/00* (2018.01)

(58) Field of Classification Search
CPC ................................. A61K 35/16; A61K 35/19
See application file for complete search history.

(56) References Cited

U.S. PATENT DOCUMENTS

| | | | |
|---|---|---|---|
| 9,199,007 B2 | 12/2015 | Julián et al. | |
| 2009/0203632 A1 | 8/2009 | Avelar et al. | |
| 2010/0196497 A1 | 8/2010 | Lim et al. | |
| 2011/0142793 A1* | 6/2011 | Chan | A61K 38/363 424/85.1 |
| 2021/0153997 A1 | 5/2021 | Limem et al. | |
| 2021/0346587 A1 | 11/2021 | Turzi | |
| 2022/0313739 A1 | 10/2022 | Mishra | |

FOREIGN PATENT DOCUMENTS

| | | |
|---|---|---|
| RU | 2675019 C1 | 12/2018 |
| RU | 2699963 C1 | 9/2019 |
| WO | 2010142784 A2 | 12/2010 |
| WO | 2020049445 A1 | 3/2020 |

OTHER PUBLICATIONS

Zumarán et al. "The 3 R's for Platelet-Rich Fibrin: A "Super" Tri-Dimensional Biomaterial for Contemporary Naturally-Guided Oro-Maxillo-Facial Soft and Hard Tissue Repair, Reconstruction and Regeneration"Materials 2018, 11, 1293; 15 pages (Year: 2018).*
Dlab et al. "Fluid Platelet-Rich Fibrin (PRF) Versus Platelet-Rich Plasma (PRP) in the Treatment of Atrophic Acne Scars: A Comparative Study" Archives of Dermatological Research (2023) 315:1249-1255 (Year: 2023).*
Ehrenfest et al. "Classification of platelet concentrates: from pure platelet-rich plasma (P-PRP) to leucocyte- and platelet-rich fibrin (L-PRF)" Trends in Biotechnology vol. 27 No. 3, p. 158-167, 2009 (Year: 2009).*
Xue et al. "Evaluation of injectable platelet-rich fibrin produced by a simple twice-centrifugation method combined with vacuum sealing drainage technology in the treatment of chronic refractory wounds" Front. Bioeng. Biotechnol., Oct. 27, 2022, vol. 10, 2022, 10 pages (Year: 2022).*
Feusi, Oscar, et al. "Platelet-rich plasma as a potential prophylactic measure against frozen shoulder in an in vivo shoulder contracture model." Archives of orthopaedic and trauma surgery (2020): 363-372.
Pixley, Jessica N., et al. "A comprehensive review of platelet-rich plasma for the treatment of dermatologic disorders." Journal of Dermatological Treatment 34.1 (2023): 2142035.
Woo, Peak. "Platelet-rich plasma in treatment of scar, atrophy, and sulcus: Short-and long-term results." Laryngoscope Investigative Otolaryngology. (2023) 1304-1311.
Harna, Bushu, et al. "Current Role of Intra-Articular Injections of Platelet-Rich Plasma in Adhesive Capsulitis of Shoulder: A Systematic Review." Bioengineering 10.1 (2022): 21.
Haider, Syed Imran, et al. "Role of Platelet-Rich Plasma in the Treatment of Adhesive Capsulitis: A Prospective Cohort Study." Cureus 14.10 (2022).
Schlesinger, S. Larry, et al. "Zafirlukast (Accolate): a new treatment for capsular contracture." Aesthetic Surgery Journal 22.4 (2002): 329-336.
FaceMed Store; "What to Know About PRP Treatments for Breast Augmentation"; 1-14. https://facemedstore.com/prp-treatments-for-breast-augmentation.
Sunshine Health Care Center; "PRP Breast Enhancement"; 1-4. https://sunshinehealth.net/health-care-services/aesthetic-medicine/prp-breast-enhancement/.
Guimier, Eugénie, et al. "Pharmacological approaches for the prevention of breast implant capsular contracture." journal of surgical research 280 (2022): 129-150.
Malahias, M., et al. (2016), A literature review and summary of capsular contracture: An ongoing challenge to breast surgeons and their patients, International Journal of Surgery Open, vol. 3 (2016) pp. 1-7.
Susini, Pietro, et al. (2023), Advances on Capsular Contracture—Prevention and Management Strategies: A Narrative Review of the Literature, PRS Global Open. Jun. 9, 2023;11(6):e5034.

(Continued)

*Primary Examiner* — Thane Underdahl

(74) *Attorney, Agent, or Firm* — ArentFox Schiff, LLP

(57) ABSTRACT

Methods and products for treating capsular contractures of breast implants including (1) platelet-rich fibrin (PRF) fraction from a patient who exhibits capsular contracture of a breast implant; and (2) applying the PRF fraction to said capsular contracture, thereby relaxing the capsular contracture.

20 Claims, 2 Drawing Sheets

(56)  References Cited

OTHER PUBLICATIONS

Owen T. M. Chan, Sarah Squire and S. Larry Schlesinger "Platelet-Rich Plasma as a Novel, Non-invasive Method to Treat Breast Capsular Contractures: a Case Report" Case Reports in Plastic Surgery and Hand Surgery 2024, vol. 11, No. 1, 2400138 (Year: 2024).

English Translation of RU2675019 C1 , 5pgs, copywrite 2025 (Year: 2025).

\* cited by examiner

USE OF PLATELET-BASED PRODUCTS FOR TREATMENT OF CAPSULAR CONTRACTURE PROXIMATE BREAST IMPLANT

CROSS-REFERENCE TO RELATED APPLICATION

This application is a continuation of U.S. application Ser. No. 19/048,619, filed Feb. 7, 2025, which claims the benefit of U.S. Provisional Patent Application No. 63/550,913, filed Feb. 7, 2024 and hereby incorporates by reference herein the contents of this application.

FIELD OF THE TECHNOLOGY

Aspects of the present disclosure relate to the use of platelet-based products, such as platelet-rich plasma (PRP) or platelet-rich fibrin (PRF), to treat, for example, capsular contracture proximate a breast implant.

BACKGROUND

When foreign bodies, such as breast implants, are present in the soft tissue of a patient, the patient undergoes an immune response to the presence of the breast implant and forms a collagenous capsule surrounding the breast implant. Normally, the capsule does not have any adverse effects on the patient. However, in some instances, for example, due to sustained inflammation, the capsule becomes fibrotic, which can lead to contraction of the capsule. Capsular contractures can cause significant pain and deformity around the breast implant. These contractures can occur anytime between shortly after a breast implant surgery to years after a breast implant surgery (interchangeably referred to herein as a breast augmentation procedure). Capsular contractures are described in more detail in Malahias, M., et al. (2016), A literature review and summary of capsular contracture: An ongoing challenge to breast surgeons and their patients, *International Journal of Surgery Open*, Vol. 3 (2016) pages 1-7 and Susini, Pietro, et al. (2023), Advances on Capsular Contracture—Prevention and Management Strategies: A Narrative Review of the Literature, *PRS Global Open*. 2023 Jun. 9; 11(6):e5034, both of which are incorporated by referenced herein.

Capsular contractures are typically measured according to the Baker Classification, which is summarized as follows: Grade 1—breast is normally soft and looks natural; Grade 2—breast is a little firm, but looks normal; Grade 3—breast is firm and looks abnormal (visible distortion); and Grade 4—breast is hard, painful, and looks abnormal (greater visible distortion). Grade 3 and Grade 4 capsular contractures typically require surgical/medical intervention for correction.

Conventionally, capsular contracture is treated surgically by either a capsulectomy or capsulotomy with or without implant exchange. In a capsulectomy, the capsule around the implant is fully removed. In a capsulotomy, the capsule is released (e.g., via incision) and/or partly removed to make more space for the implant.

SUMMARY OF THE DISCLOSURE

The disclosure provides methods for treating capsular contractures of breast implants comprising (1) obtaining a platelet-based product such as the platelet-rich plasma or protein-rich plasma (PRP) or platelet-rich fibrin (PRF) fraction of blood from a patient who exhibits capsular contracture of a breast implant; and (2) applying the platelet-based product fraction to said capsular contracture, thereby relaxing the capsular contracture. In one aspect of the disclosure, the platelet-based product is applied to the capsular contracture by injecting the platelet-based product adjacent to the capsular contracture and spreading the injected platelet-based product under the skin by manipulation with or without application of acoustic sound waves, for example, by a Sonicator 740™ instrument (by Mettler Electronics of Anaheim, CA), to promote relaxation of the contracture. In some aspects, other devices producing similar sound waves can also be used. In another mode, the disclosure provides a methods for treating capsular contracture of breast implants comprising (1) obtaining a platelet-based product from a patient who exhibits capsular contracture of a breast implant; and (2) applying the platelet-based product to the patient's skin adjacent to said capsular contracture and inducing the transdermal absorption of the platelet-based product into the skin with pulsed electric currents, thereby relaxing the capsular contracture. The pulsed currents may be supplied, for example, by a Collagenizer NEO™ instrument produced by Collagenizing of Basel, Switzerland. The platelet-based product may be administered to the patient on a single treatment session, or multiple treatment sessions separated by several days to weeks; individual administrations may be by injection or by transdermal absorption, and the form of administration may be the same or different for successive occasions. Typically, the temporal separation between successive occasions will be from one week to 25 days. Preferably, the patient's capsular contracture exhibits a Baker score grade of 3-4 prior to application of the platelet-based product, and relaxation of the capsular contracture by at least one level Baker score grade occurs within 30 days of the application.

The disclosure also provides a platelet-based product for use in relaxing capsular contractures associated with a breast implant, the platelet-based product being isolated from whole blood of a patient who exhibits capsular contracture of a breast implant, and where application of the product into the capsular contracture adjacent to the breast implant of the patient promotes relaxation of the capsular contracture. The disclosure also provides a method of preparing a product suitable for treatment of capsular contracture of a breast implant in a patient, the method comprising creating platelet-rich plasma (PRP) or platelet-rich fibrin (PRF) from whole blood, wherein the whole blood was obtained from the patient who exhibits capsular contracture of a breast implant. The product of this disclosure, or the product produced by the method of this disclosure is suitable for use in any mode of the method of this disclosure described in the previous paragraph. The product of this disclosure is autologous to the patient treated by any method of this disclosure.

In some aspects, capsular contractures involving breast implants are assessed via contracture testing. Such contractures are then treated with the platelet-based product based on the results of the testing. In some aspects, methods for conducting contracture testing include excision of contracture tissue or removal of fluid adjacent to the implant with a needle. Then, this material can be tested for characteristics, in some aspects, which include but are not limited to, collagen fiber density, fibroblast count, myofibroblast count, and immune cell characterization, fibrinogen, fibrin, or calcium. Additionally, the method includes assessment of the location and architecture of the contracture by ultrasound characterization. These collective testing results can be utilized to determine the appropriate downstream treatment modality.

Additional advantages and novel features of these aspects will be set forth in part in the description that follows, and in part will become more apparent to those skilled in the art upon examination of the following and learning by practice of the disclosure.

DETAILED DESCRIPTION

Aspects of the present disclosure relate to the use of a platelet-based product to treat capsular contractures surrounding at least a portion of a breast implant by administering a platelet-based product to a patient having the capsular contracture.

The methods and products described in the present disclosure are described with regard to patients having at least one breast implant.

The method and products described in the present disclosure are intended to treat a patient having capsular contracture surrounding at least a portion of a breast implant by administering a platelet-based product to the capsular contracture. The capsular contracture treated according to this disclosure is preferably a Grade 3 or Grade 4 capsular contracture surrounding a breast implant.

The platelet-based product is a blood product that is made from a whole blood aliquot. The platelet-based product types include the platelet-rich plasma (PRP) or platelet-rich fibrin (PRF) fraction of blood.

Figure 1:
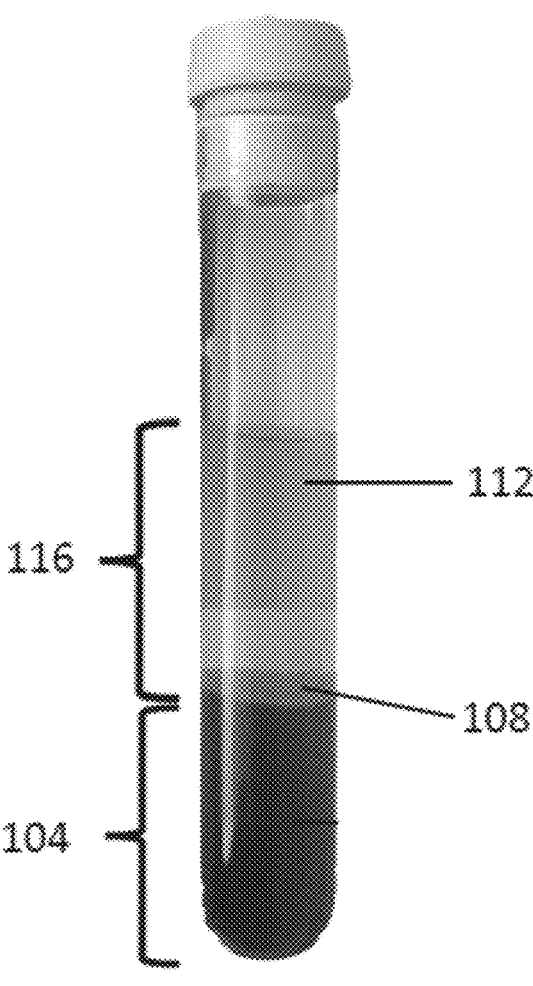
FIG. 1 illustrates an example whole blood sample that has been separated into layers via centrifugation.

Platelet-rich plasma (PRP) is produced by centrifuging the whole blood in a tube with an anticoagulant, in order to separate the red blood cells ("RBCs") from the platelets and the plasma. In some aspects, the whole blood sample may be centrifuged at approximately 3000-4000 rpm for approximately 10-15 minutes. In some aspects, the whole blood sample may be centrifuged at approximately 3500 rpm for approximately 10-12 minutes. Methods for fractionating whole blood via centrifugation are well-known, and the skilled person will have no trouble performing this separation to obtain an appropriate fraction. As shown in FIG. 1, the blood is separated into three layers by centrifugation—a lower layer 104 containing RBCs, a middle layer 108 including platelets, and an upper layer 112 including the plasma. As referred to herein, the "platelet layer" typically includes non-RBC components. The platelet 108 and plasma layers 112 (e.g. fractions) are retrieved to form the platelet-based product 116. The PRP is rich in platelets, fibrinogen, fibrin, chemokines, leukocytes, and platelet contents. The platelet contents may include platelet-derived growth factor (PDGF), vascular endothelial growth factor VEGF), epithelial growth factor, transforming growth factor beta (TGF-β), insulin-like growth factor (IGF), serotonin, dopamine, histamine, adenosine, and calcium. See Pixley, Jessica N. et al. (2023), A comprehensive review of platelet-rich plasma for the treatment of dermatologic disorders, *Journal of Dermatological Treatment*, Vol. 34, No. 1, 2214-2035. The exemplary process of preparing the PRP product described in the present disclosure does not include any additives; however, additives may be incorporated to the PRP product within the contemplation of this disclosure. In certain circumstances, calcium chloride or other substances that trigger platelet activation and fibrin polymerization may be added.

For the generation of PRP, in some aspects, the PRP product may include a chelator and/or a buffer to serve as an anticoagulant. The chelator may be present in an amount sufficient to sequester calcium ions found in the blood, thereby inhibiting clotting of the blood. For example, in some aspects, during production of the PRP product, an acid citrate dextrose ("ACD") solution may be added to the whole blood. Typical ACD solution includes approximately 22.0 grams per liter (g/L) trisodium citrate, approximately 8 g/L citric acid, and approximately 24.5 g/L dextrose. In some aspects, approximately 1.5 milliliters (mL) of the ACD solution and 6 mL of whole blood from the patient is used to form the PRP product. In some aspects, the ACD may have a pH of 5.0. In some aspects, approximately 1.5 mL of the ACD solution and up to 6 mL of the whole blood from the patient is used to form the PRP product. In an exemplary mode, the patient's blood is collected in an 8.5 mL vial containing approximately 1.5 mL of ACD, such as Vacutainer™ tubes including ACD Solution A produced by Becton, Dickinson, and Company of Franklin Lakes, New Jersey, U.S.A.

Platelet-rich fibrin (PRF) is produced by centrifuging the whole blood in a tube without anticoagulant, in order to separate the red blood cells ("RBCs") from the platelets and the plasma. Without anticoagulation, a semi-solid clot with a fibrin scaffold is formed that can be removed and cut away from the red blood cells. In some aspects, the whole blood sample may be centrifuged at approximately 700 rpm for approximately 3 minutes. In some aspects, the whole blood sample may be centrifuged at approximately 1500 rpm for approximately 14 minutes. In some aspects, the whole blood sample may be centrifuged at approximately 2700 rpm for approximately 12 minutes. In some aspects, the whole blood sample may be centrifuged at approximately 3300 rpm for approximately 2 minutes. In some aspects, the whole blood sample may be centrifuged at approximately 3000-4000 rpm for approximately 10-15 minutes. In some aspects, the whole blood sample may be centrifuged at approximately 3500 rpm for approximately 10-12 minutes. Methods for fractionating whole blood via centrifugation are well-known, and the skilled person will have no trouble performing this separation to obtain an appropriate fraction. Without anticoagulation, a semi-solid clot with a fibrin scaffold is formed that contains platelets, platelet contents, leukocytes, stem cells, chemokines, fibronectin, vitronectin, and other growth factors. The platelet contents may include platelet-derived growth factor (PDGF), vascular endothelial growth factor VEGF), epithelial growth factor, transforming growth factor beta (TGF-β), insulin-like growth factor (IGF), serotonin, dopamine, histamine, adenosine, and calcium. See Miron, Richard J. et al. (2023), Optimization of platelet-rich fibrin, *Periodontology*, Vol. 94, 799-91. In some aspects, the exemplary process of preparing the PRF product described in the present disclosure does not include any additives. In other aspects, additives may be incorporated to the PRF product. For example, in some circumstances, calcium chloride or other substances that trigger platelet activation and fibrin polymerization may be added.

For the generation of PRF, the patient's blood is collected in a tube without anticoagulant. In some aspects, the blood is collected in a hydrophilic tube made from plain glass or silica-coated plastic. In some aspects, the blood is collected in a hydrophobic tube made from polyethylene terephthalate plastic. In an exemplary mode, the patient's blood is collected in an 8.5 mL vial, such as Vacutainer™ tubes without additives produced by Becton, Dickinson, and Company of Franklin Lakes, New Jersey, U.S.A.

In some aspects, the platelet-based products may include additional components which do not interfere with the platelet-based product's effect on the capsular contracture. Such components may include, for example, sterile water, dextrose, sodium chloride, etc. In some aspects, the platelet-based product may include one or more analgesic compositions.

As used herein, the whole blood used to produce the platelet-based product comes from the patient to be treated, so the platelet-based product is an autologous product. Therefore, the patient's immune system will not react to the platelet-based product.

After the platelet-based product has been produced, the platelet-based product is typically applied to the patient's capsular contracture. In some aspects, the platelet-based product is applied to at least a portion of the patient's capsular contracture on the same day as the platelet-based product is prepared.

In some aspects, ultrasound data of the patient's capsular contracture may be used to identify a location of the patient's capsular contracture and/or to determine a location of the patient's implant relative to the capsular contracture may be determined. The ultrasound data may be used by the practitioner to determine a suitable location on the patient for applying the platelet-based product, so that the platelet-based product is applied near the patient's contracture. In some aspects, the ultrasound data may be used to prevent damage to the implant. For example, in aspects in which the platelet-rich product is injected into the patient, the ultrasound data may be used to select an injection site.

In some aspects, the platelet-based product is applied to the patient's capsular contracture by injecting the platelet-based product into or adjacent the patient's capsular contracture. In some aspects, the skin overlying a portion of the patient's capsular contracture may be nicked with a scalpel and the platelet-based product may then be delivered to or near the patient's capsular contracture via a blunt needle or cannula. In some aspects, the platelet-based product may be injected approximately 4-6 millimeters (mm) below the patient's skin. In some aspects, the platelet-based product may be injected approximately 1.5 mm below the patient's skin. The patient's capsular contracture may then be manually manipulated to encourage the platelet-based product to diffuse throughout the patient's capsular contracture. In some aspects, the patient's capsular contracture may then be manually manipulated in combination with the addition of acoustic sound waves may be applied encourage the platelet-based product to diffuse throughout the patient's capsular contracture. In some aspects, the patient's capsular contracture may then be manually manipulated in combination with the addition of ultrasound waves may be applied encourage the platelet-based product to diffuse throughout the patient's capsular contracture. In such aspects, the ultrasound waves may have frequencies of about 1 megahertz (MHz) to about 3 MHz. In some aspects, 3 to 25 mL of platelet-based product may be injected into the patient per treatment session. In some aspects, as much as 18 mL or more of the platelet-based product may be injected into the patient per treatment session. In some aspects, the platelet-based product is typically injected to treat capsular contractures that are difficult to relax. For example, injection is typically used in conditions in which the capsular contraction is very firm (e.g., a Baker grade of 4) and/or if the capsular contracture is well below the patient's skin (e.g., at least 1 to 1.5 cm below the patient's skin). The platelet-based product may be applied to the patient via injection in one to five treatment sessions.

In some aspects, the platelet-based product is applied to the patient's skin adjacent and/or overlying at least a portion of the patient's capsular contracture. A pulsed electrical current is then applied to the patient's skin to transdermally deliver the platelet-based product to or adjacent the patient's capsular contracture. In some aspects, a suitable device to provide the pulsed current is the Collagenizer NEO™. The skilled person will understand that devices having similar transdermal effects can also be used. In some aspects, 3 to 25 mL of the platelet-based product may be applied to the patient per treatment session. In some aspects, 3 to 18 mL of the platelet-based product may be applied to the patient per treatment session. In such aspects, up to 18 mL of the platelet-based product may be applied to the patient per treatment session. The platelet-based product may be applied to the patient in one to five treatment sessions.

The amount of the platelet-based product administered to a patient may vary based on the size of the patient's implants and/or the Baker grade of the capsular contracture. In some aspects, approximately 3.5 mL to approximately 25 mL of the platelet-based product can be administered to the patient per treatment session. In some aspects, approximately 3.5 mL to approximately 18 mL of the platelet-based product can be administered to the patient per treatment session. In some aspects, approximately 3.5 mL to approximately 9 mL of the platelet-based product can be administered to the patient per treatment session. In some aspects, approximately 6 mL to 9 mL can be administered to the patient per treatment session. In some aspects, the patient undergoes one or more treatments with the platelet-based product. In some aspects, the first treatment session may include applying the platelet-based product to the patient transdermally. In such aspects, the second treatment session may include applying the platelet-based product to the patient by injection or applying the platelet-based product to the patient transdermally. In some aspects, the first treatment session may include applying the platelet-based product to the patient by injection. In such aspects, the second treatment session may include applying the platelet-based product to the patient by injection or applying the platelet-based product to the patient transdermally. In some aspects, an amount of platelet-based product used can be determined based on one or more characteristics of the contracture. Example characteristics include an amount of time that the patient had the capsular contracture, a thickness and/or amount of layers of the contracture, a depth of the capsular contracture below the skin, and so forth.

After the platelet-based product has been applied to the patient, the platelet-based product will promote relaxation of the patient's capsular contracture. In some aspects, the relaxation of the patient's capsular contracture occurs as early as the same day as the platelet-based product has been applied to the patient. Typically, relaxation can be observed after a week or more, up to several weeks. Relaxation of the capsular contracture is typically permanent. However, in some aspects, a touch-up treatment may be completed every six to eighteen months. As used herein, "relaxing" refers to relaxing the contracture, dissolving the contracture, causing breakdown of the contracture, loosening the contracture, and so forth.

In some aspects, the patient may receive multiple treatments with the platelet-based product. In such aspects, the patient's first treatment may include transdermal application of the platelet-based product; and the patient's second treatment may include application of the platelet-based product to the patient via injection, or the order of treatment may be reversed. In aspects in which the patient receives more than one application of the platelet-based product, a subsequent application of the platelet-based product is provided about one week to two months, three weeks to one month, or, preferably, 21-25 days after a prior application of the platelet-based product. In some aspects, the platelet-based product is applied to the patient on at least two occasions in a 25 day period.

In preferred aspects, relaxation of the capsular contracture by at least one Baker grade occurs within 30 days of the application of the platelet-based product to the patient.

In some aspects, the treatments may continue until pain felt by the patient at or near the implant site has been reduced, the patient's breasts become symmetric, the breast tissue softens to at least a Baker grade of 2, and/or the patient is satisfied with the appearance and thickness (e.g., softness) of the breast tissue. For example, the treatments may stop after visible distortion of the breast tissue and/or the implant has been reduced. In some aspects, the treatments may stop after a decrease in the patient's pain relative to the patient's pain before treatment started. For example, patients are asked to grade their pain on a scale of 0-4 before treatment begins and after they have received treatment with the platelet-based product as described herein. In some aspects, the treatments may stop after the patient has experienced a decrease in firmness, for example a decrease in the Baker grade of the contracture. In some aspects, the treatment may stop after the patient has experienced a reduction of visible distortion.

In some aspects, the patient is 20 years old and older. In some aspects, the patient is 30 years old and older. In some aspects, the patient is 40 years old and older. In some aspects, the patient is 50 years old and older. In some aspects, the patient is 60 years old and older. In some aspects, the patient is 70 years old and older. In some aspects, the patient is 80 years old and older. In some aspects, the patient's capsular contracture has experienced a decrease in Baker grade since the initial treatment. In some aspects, the patient has experienced a decrease in pain in the area of the implant since the initial treatment. In some aspects, the patient has experienced a decrease in distortion in the area of the implant since the initial treatment.

Aspects of the present disclosure may include pre-treatment testing of the breast contracture to guide subsequent therapy. In some aspects, contracture tissue or tissue around the contracture may be obtained by an incision of the skin and subsequent deeper biopsy of the contracture for analysis of myofibroblasts and/or immune cell characterization by conventional histologic analysis to determine characterization data. In such aspects, the myofibroblast and/or immune cell characterization data may be compared to one or more predefined thresholds to determine a severity of capsular contracture. In some aspects, the severity of the capsular contracture may include the Baker grade of the capsular contracture. In some aspects, multiple thresholds corresponding to different Baker grades of capsular contractures may be used. In some aspects, the fluid surrounding the contracture may be withdrawn by a needle and syringe for analysis of immune cells by conventional flow cytometry or characterization of the analytes of fibrinogen and/fibrin, by conventional clinical pathologic methods to determine characterization data. In such aspects, characterization data of the analytes of fibrinogen and/or fibrin may be compared to one or more predefined thresholds to determine the severity of the capsular contracture. In some aspects, multiple thresholds corresponding to different Baker grades of capsular contractures may be used. In some aspects, the location and architecture of the capsular contracture can be assessed by ultrasound characterization. For example, the depth of the capsular contracture beneath the skin may be determined by ultrasound. In some aspects, the pre-treatment testing described herein may be used to determine an amount of platelet-based product that should be used in the treatment session. In some aspects, the pre-treatment testing described herein may be used to determine a number of additional treatments that may be needed to treat the contracture.

In some aspects, progression of the treatment may be determined using the methods described above with regard to pre-treatment testing.

Figure 2:
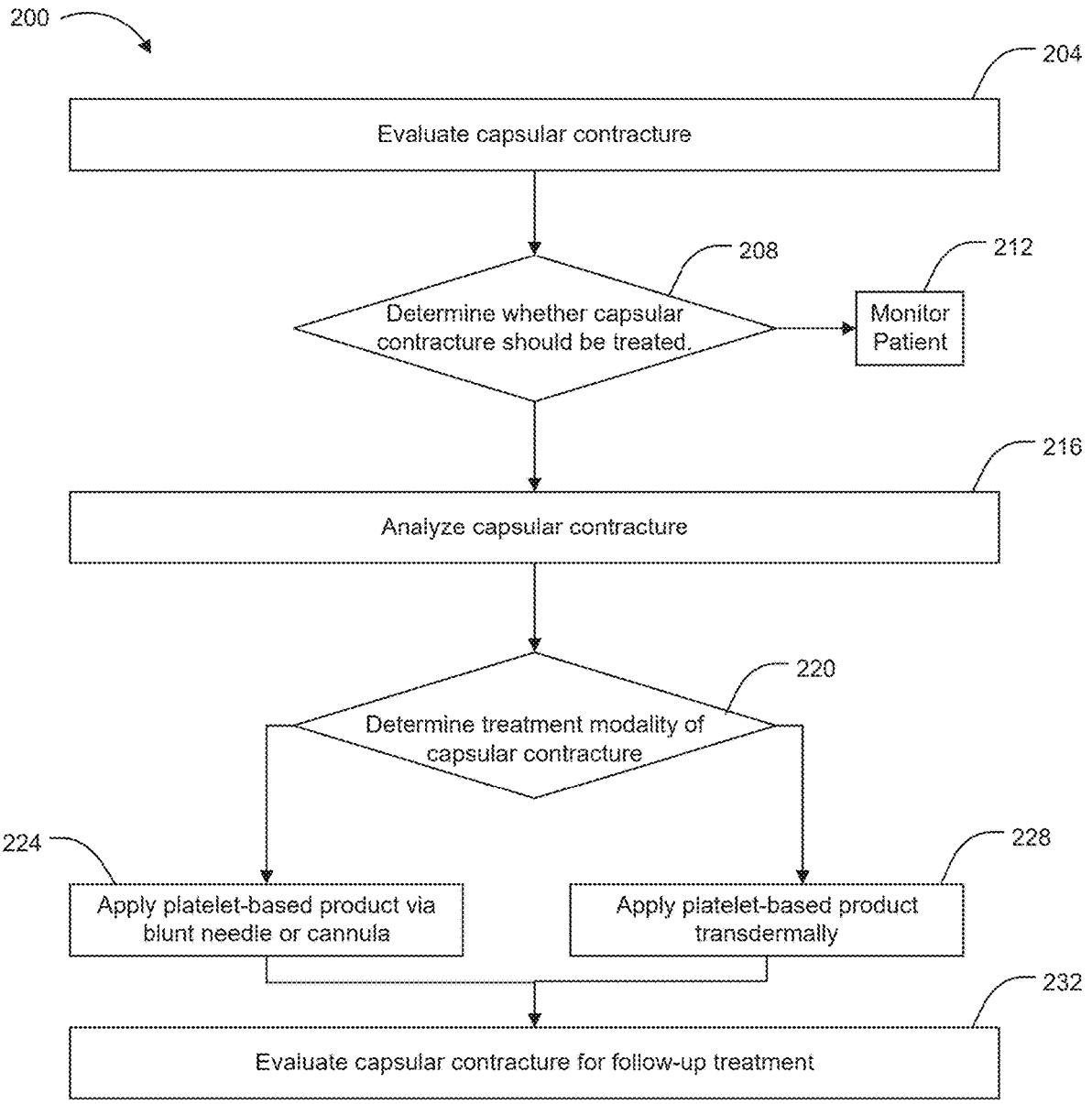
FIG. 2 illustrates a schematic representation of a process of treating capsular contractures surrounding at least a portion of a breast implant using platelet-based products according to an aspect of the present disclosure.

FIG. 2 illustrates an example method 200 for preparing the platelet-based product and applying the platelet-based product to the capsular contracture surrounding at least a portion of a breast implant using platelet-based products according to an aspect of the present disclosure is evaluated.

At 204, the capsular contracture is evaluated. For example, the Baker grade of the contracture may be determined. In another example, the patient may be asked to rate an amount of pain associated with the contracture on a scale of 0 to 4, with 0 being no pain, and 4 being a high amount of pain.

At 208, a determination is made as to whether the contracture should be treated. In some aspects, the determination may be made based on the Baker score and/or other criteria, such as patient pain. In aspects in which the contracture should not be treated, the patient may be monitored, as shown by 212.

At 216, the capsular contracture may be analyzed. For example, in some aspects, ultrasound data may be used to determine a location, architecture, and/or a thickness of the capsular contracture. In some aspects, contracture tissue or tissue around the contracture may be obtained by an incision of the skin and subsequent deeper biopsy of the contracture for analysis of myofibroblasts and/or immune cell characterization by conventional histologic analysis. In such aspects, the collagen fiber density and/or myofibroblast and/or immune cell characterization data may be compared to one or more predefined thresholds to determine a severity of capsular contracture. In some aspects, the severity of the capsular contracture may include the Baker grade of the capsular contracture. In some aspects, the fluid surrounding the contracture may be withdrawn by a needle and syringe for analysis of immune cells by conventional flow cytometry or characterization of the analytes of fibrinogen and/fibrin, by conventional clinical pathologic methods. In such aspects, the immune cell data or characterization of the analytes of fibrinogen and/or fibrin may be compared to one or more predefined thresholds to determine the severity of the capsular contracture.

At 220, a treatment modality may be determined. The treatment modality may be determined based on the data determined at 216. The treatment modality may include an amount of platelet-based product to apply to the patient and/or an application location for the platelet-based product. Determining the treatment modality may include determining how the platelet-based product should be applied to the patient. For example, in some aspects, as shown at 224, the platelet-based product may be applied via a blunt needle or cannula. In such aspects, the patient's capsular contracture may then be manually manipulated, either alone or in combination with the acoustic sound waves and/or ultrasound waves. In some aspects, as shown at 228, the platelet-based product may be applied transdermally.

At 232, the capsular contracture may be evaluated for follow-up treatment.

EXAMPLES

The exemplary platelet-based product is obtained by drawing whole blood from the patient to be treated into (1) one or more sterile glass evacuated blood collection vials which already contain acid citrate dextrose (pH=5.0) for PRP generation or (2) one or more sterile glass evacuated blood collection vials which lack anticoagulation for PRF generation. Collected blood vials are centrifuged to sediment red blood cells. The layers containing plasma and platelets are recovered, leaving the RBC in the tube. The combined plasma and platelet layers form the platelet-based product and are administered to the patient from whom the whole blood was drawn on the day that the platelet-based product is prepared.

Patient 1

Patient 1 is a 41 year old female with two prior bilateral breast augmentation procedures. The most recent breast augmentation procedure was 1.2 years ago (silicone breast implants, left and right 700 mL volume implants). Patient 1 developed a capsular contracture on the right side having a Baker grade of 4 out of 4. After two treatments with the PRP product applied via injection (approximately 7 mL of the PRP product applied per treatment session), the capsular contracture decreased to a Baker grade of 2.5 out of 4, as observed 21 days after the first application.

Patient 2

Patient 2 is a 46 year old female with three prior bilateral breast augmentation procedures. The most recent breast augmentation procedure was 1.7 years ago (silicone breast implants, left 800 mL volume implant, right 695 mL volume implant). Patient 2 developed a capsular contracture on the right side having a Baker grade of 3 out of 4. After four applications of PRP product, including three applications via injection and one transdermal application via Collagenizer NEO™ therapy (approximately 17.5 mL of PRP product applied for the treatment session), the capsular contracture decreased to a Baker grade of 2 out of 4, as observed 133 days after the first application.

Patient 3

Patient 3 is a 33 year old female with a bilateral breast augmentation procedure. The breast augmentation procedure was 0.6 years ago (silicone implants, left and right 535 mL volume implants). Patient 3 developed a capsular contracture on the right side having a Baker grade of 3 out of 4. After one treatment with PRP product applied via injection and one treatment with PRP product applied transdermally via Collagenizer NEO™ therapy (14 mL of PRP product applied per treatment session), the contracture decreased to a Baker grade of 2 out of 4, as observed 44 days after the first application.

Patient 4

Patient 4 is a 36 year old female with a history of a prior, bilateral, dual plane breast augmentation with silicone implants (left and right 535 mL volume implants). Subsequently, the right implant was removed and replaced with a new 535 mL volume implant due to asymmetry. Patient 4 developed a capsular contracture with a Baker grade of 3-4 out of 4 on the right side after about 9.6 months. After three treatments with PRP product applied transdermally via Collagenizer NEO™ therapy (9 mL of PRP product applied for the first treatment session, 18 mL of PRP product applied for the second treatment session, and 9 mL of PRP product applied for the third treatment session), the contracture decreased to a Baker grade of 1-2 out of 4, as observed nine weeks after the first application.

Patient 5

Patient 5 is a 45 year old woman with a history of prior, bilaterial breast augmentation status-post removal. Patient 5 subsequently had a bilateral, dual plane breast augmentation with silicone implants (left and right-535 mL). After 6 months, Patient 5 developed firmness on the right side. Treatment was initiated using ultrasound therapy and Zafirlukast, but the firmness continued to progress. After 1.7 years, Patient 5 had a capsular contracture on the right side with a Baker grade of 3 out of 4, and asymmetry, with the right side higher than the left. After six treatments with PRP product applied transdermally via Collagenizer NEO™ therapy (9 mL of PRP product applied for the first three treatment sessions and 6 mL of PRP product applied for the fourth through sixth treatment sessions), the contracture decreased to a Baker grade of 1-2 out of 4 and symmetry improved, as observed fourteen weeks after the first application.

The approach described for Patients 1-5 is not intended to be limiting. Similar approaches can be used for applying the platelet-based product to other patients having capsular contracture.

All patent and non-patent literature publications mentioned above are hereby incorporated by reference herein in their entireties.

While the aspects described herein have been described in conjunction with the examples above, the skilled person will understand that various alternatives, modifications, variations, and improvements may be made in the procedure without departing from the spirit of this disclosure. Accordingly, the examples, as set forth above, are intended to be illustrative, not limiting.

Specific Aspects

The disclosure provides for the following specific aspects (numbered below):

1. A method for treating capsular contracture of breast implant comprising (1) obtaining a platelet-rich plasma (PRP) fraction from a patient who exhibits capsular contracture of a breast implant; and (2) applying the PRP fraction to said capsular contracture, thereby relaxing the capsular contracture; or treating capsular contracture of breast implant comprising applying a PRP fraction obtained from a patient who exhibits capsular contracture of a breast implant to said capsular contracture, thereby relaxing the capsular contracture.

2. The method of aspect 1, wherein the PRP fraction is applied to the capsular contracture by injecting the PRP fraction adjacent to the capsular contracture and spreading the injected PRP fraction under a patient's skin by manipulation to promote relaxation of the capsular contracture.

3. The method of aspect 2, wherein acoustic sound waves or ultrasound waves are applied during the manipulation.

4. The method of aspect 2, wherein the PRP fraction is a first PRP fraction and wherein a subsequent PRP fraction is obtained from the patient and the subsequent PRP fraction is applied to the capsular contracture by applying the subsequent PRP fraction to the patient's skin adjacent to said capsular contracture and inducing transdermal absorption of the subsequent PRP fraction into the skin through pulsed electrical currents, thereby relaxing the capsular contracture.

5. The method of aspect 1, wherein applying the PRP fraction to said capsular contracture includes applying the PRP fraction to a patient's skin adjacent to said capsular contracture and inducing transdermal absorption of the PRP fraction into the skin with pulsed electrical currents, thereby relaxing the capsular contracture.

6. The method of aspect 5, wherein a device placed proximally to the skin provides the pulsed electrical currents.

7. The method of aspect 5, wherein the PRP fraction is a first PRP fraction and wherein a subsequent PRP fraction is obtained from the patient and the subsequent PRP fraction is applied to the capsular contracture by applying the subsequent PRP fraction to the skin by injecting the subsequent PRP fraction adjacent to the capsular contracture and spreading the injected subsequent PRP fraction under the skin by manual manipulation to promote relaxation of the capsular contracture.

8. The method of aspect 7, wherein acoustic sound waves or ultrasound waves are applied during the manipulation.

9. The method of aspect 5, wherein the PRP fraction is a first PRP fraction and wherein a subsequent PRP fraction is obtained from the patient and the subsequent PRP fraction is applied to the capsular contracture by applying the subsequent PRP fraction to skin adjacent to said capsular contracture and inducing the transdermal absorption of the subsequent PRP fraction into the skin through pulsed electrical currents, thereby relaxing the capsular contracture.

10. The method of any one of aspects 1 to 9, wherein the PRP fraction is a first PRP fraction and wherein a subsequent PRP fraction is obtained from the patient, and wherein a subsequent application of PRP is applied to the capsular contracture at least one week after the first PRP fraction is applied to the capsular contracture.

11. The method of any one of aspects 1-9, wherein the PRP fraction is a first PRP fraction and wherein a subsequent PRP fraction is obtained from the patient, and wherein a subsequent application of PRP is applied to the capsular contracture within a 25 day period of the first PRP fraction.

12. The method of any one of aspects 1-9, wherein the capsular contracture exhibits a Baker grade of 3-4 prior to application of the PRP fraction, and inhibition of the capsular contracture by at least one level Baker grade occurs within 30 days of the application.

13. The method of aspect 1, wherein the PRP fraction is applied by injection in a first treatment session and transdermally in at least one subsequent treatment session.

14. The method of any one of aspects 1-13, wherein successive treatment sessions are separated by from one week to 25 days.

15. The method of any one of claims 1-14, wherein myofibroblasts and/or immune cells are obtained from the capsular contracture, and a severity of the capsular contracture is based on data determined from a biopsy of the myofibroblasts and/or immune cells.

16. The method of any one of aspects 1-14, wherein myofibroblasts and/or immune cells are obtained from the capsular contracture, and a treatment volume of the PRP fraction is determined based on data determined from a biopsy of the myofibroblasts and/or immune cells.

17. The method of any one of aspects 1-14, wherein fibrinogen and/or fibrin are obtained from fluid surrounding the capsular contracture, and a severity of the capsular contracture is based on data determined based on characteristics of the fibrinogen and/or fibrin.

18. The method of any one of aspects 1-14, wherein fibrinogen and/or fibrin are obtained from fluid surrounding the capsular contracture, and a treatment volume of the PRP fraction is determined based on data determined from a biopsy of the fibrinogen and/or fibrin.

19. The method of any one of aspects 1-18, wherein an application location for the PRP fraction is determined based on ultrasound data of the capsular contracture.

20. A product comprising a platelet-rich plasma (PRP) fraction for use in relaxing capsular contractures associated with a breast implant, wherein the PRP fraction is isolated from whole blood of a patient who exhibits capsular contracture of a breast implant, and wherein application of the product into the capsular contracture adjacent to the breast implant promotes relaxation of the capsular contracture. In some aspects, the product of aspect 20 is applied to the capsular contracture of the breast implant according to any one of aspects 1-19.

21. A method of preparing a sample suitable for treatment of capsular contracture of a breast implant in a patient comprising separating a platelet-rich plasma (PRP) fraction from whole blood, wherein the whole blood was obtained from the patient who exhibits capsular contracture of a breast implant. In some aspects, the PRP fraction prepared according to the method of aspect 21 is applied to the capsular contracture of the breast implant according to any one of aspects 1-19.

22. A method for treating capsular contracture of breast implant comprising (1) obtaining a platelet-rich fibrin (PRF) fraction from a patient who exhibits capsular contracture of a breast implant; and (2) applying the PRF fraction to said capsular contracture, thereby relaxing the capsular contracture.

23. The method of aspect 22, wherein the PRF fraction is applied to the capsular contracture by injecting the PRF fraction adjacent to the capsular contracture and spreading the injected PRF fraction under a patient's skin by manipulation to promote relaxation of the capsular contracture.

24. The method of aspect 23, wherein acoustic sound waves or ultrasound waves are applied during the manipulation.

25. The method of aspect 23, wherein the PRF fraction is a first PRF fraction and wherein a subsequent PRF fraction is obtained from the patient and the subsequent PRF fraction is applied to the capsular contracture by applying the subsequent PRF fraction to the patient's skin adjacent to said capsular contracture and inducing transdermal absorption of the subsequent PRF fraction into the skin through pulsed electrical currents, thereby relaxing the capsular contracture.

26. The method of aspect 22, wherein applying the PRF fraction to said capsular contracture includes applying the PRF fraction to a patient's skin adjacent to said capsular contracture and inducing transdermal absorption of the PRF fraction into the skin with pulsed electrical currents, thereby relaxing the capsular contracture.

27. The method of aspect 26, wherein a device placed proximally to the skin provides the pulsed electrical currents.

28. The method of aspect 26, wherein the PRF fraction is a first PRF fraction and wherein a subsequent PRF fraction is obtained from the patient and the subsequent PRF fraction is applied to the capsular contracture by applying the subsequent PRF fraction to the skin by injecting the subsequent PRF fraction adjacent to the capsular contracture and spreading the injected subsequent PRF fraction under the skin by manual manipulation to promote relaxation of the capsular contracture.

29. The method of aspect 28, wherein acoustic sound waves or ultrasound waves are applied during the manipulation.

30. The method of aspect 26, wherein the PRF fraction is a first PRF fraction and wherein a subsequent PRF fraction is obtained from the patient and the subsequent PRF fraction is applied to the capsular contracture by applying the subsequent PRF fraction to the skin adjacent to said capsular contracture and inducing the transdermal absorption of the subsequent PRF fraction into the skin through pulsed electrical currents, thereby relaxing the capsular contracture.

31. The method of any one of aspects 22-30, wherein the PRF fraction is a first PRF fraction and wherein a subsequent PRF fraction is obtained from the patient, and wherein a subsequent application of PRF is applied to the capsular contracture at least one week after the first PRF fraction is applied to the capsular contracture.

32. The method of any one of aspects 22-30, wherein the PRF fraction is a first PRF fraction and wherein a subsequent PRF fraction is obtained from the patient, and wherein a subsequent application of PRF is applied to the capsular contracture within a 25 day period of the first PRF fraction.

33. The method of any one of aspects 22-30, wherein the capsular contracture exhibits a Baker grade of 3-4 prior to application of the PRF fraction, and inhibition of the capsular contracture by at least one level Baker grade occurs within 30 days of the application.

34. The method of aspect 22, wherein the PRF fraction is applied by injection in a first treatment session and transdermally in at least one subsequent the treatment session.

35. The method of any one of aspects 22-34, wherein successive treatment sessions are separated by from one week to 25 days.

36. The method of any one of aspects 22-35, wherein myofibroblasts and/or immune cells are obtained from the capsular contracture, and a severity of the capsular contracture is based on data determined from a biopsy of the myofibroblasts and/or immune cells.

37. The method of any one of aspects 22-35, wherein myofibroblasts and/or immune cells are obtained from the capsular contracture, and a treatment volume of the PRF fraction is determined based on data determined from a biopsy of the myofibroblasts and/or immune cells.

38. The method of any one of aspects 22-35, wherein fibrinogen and/or fibrin are obtained from fluid surrounding the capsular contracture, and a severity of the capsular contracture is based on data determined based on characteristics of the fibrinogen and/or fibrin.

39. The method of any one of aspects 22-35, wherein fibrinogen and/or fibrin are obtained from fluid surrounding the capsular contracture, and a treatment volume of the PRF fraction is determined based on data determined from a biopsy of the fibrinogen and/or fibrin.

40. The method of aspect 22, wherein an application location for the PRF fraction is determined based on ultrasound data of the capsular contracture.

41. A product comprising a platelet-rich fiber (PRF) fraction for use in relaxing capsular contractures associated with a breast implant, wherein the PRF fraction is isolated from whole blood of a patient who exhibits capsular contracture of a breast implant, and wherein application of the product into the capsular contracture adjacent to the breast implant promotes relaxation of the capsular contracture. In some aspects, the PRP fraction prepared according to the method of aspect 41 is applied to the capsular contracture of the breast implant according to any one of aspects 22-40.

42. A method of preparing a sample suitable for treatment of capsular contracture of a breast implant in a patient comprising separating a platelet-rich fibrin (PRF) fraction from whole blood, wherein the whole blood was obtained from the patient who exhibits capsular contracture of a breast implant. In some aspects, the PRP fraction prepared according to the method of aspect 42 is applied to the capsular contracture of the breast implant according to any one of aspects 22-40.

43. A method for treating capsular contracture of breast implant comprising applying a platelet rich fibrin (PRF) fraction obtained from a patient who exhibits capsular contracture of a breast implant to said capsular contracture, thereby relaxing the capsular contracture.

What is claimed is:

1. A method for treating capsular contracture of breast implant comprising (1) obtaining a platelet-rich fibrin (PRF) fraction from a patient who exhibits capsular contracture of a breast implant; and (2) applying the PRF fraction to said capsular contracture, thereby relaxing the capsular contracture.

2. The method of claim 1, wherein the PRF fraction is applied to the capsular contracture by injecting the PRF fraction adjacent to the capsular contracture and spreading the injected PRF fraction under a patient's skin by manipulation to promote relaxation of the capsular contracture.

3. The method of claim 2, wherein acoustic sound waves or ultrasound waves are applied during the manipulation.

4. The method of claim 2, wherein the PRF fraction is a first PRF fraction and wherein a subsequent PRF fraction is obtained from the patient and the subsequent PRF fraction is applied to the capsular contracture by applying the subsequent PRF fraction to the patient's skin adjacent to said capsular contracture and inducing transdermal absorption of the subsequent PRF fraction into the skin through pulsed electrical currents, thereby relaxing the capsular contracture.

5. The method of claim 1, wherein applying the PRF fraction to said capsular contracture includes applying the PRF fraction to a patient's skin adjacent to said capsular contracture and inducing transdermal absorption of the PRF fraction into the skin with pulsed electrical currents, thereby relaxing the capsular contracture.

6. The method of claim 5, wherein a device placed proximally to the skin provides the pulsed electrical currents.

7. The method of claim 5, wherein the PRF fraction is a first PRF fraction and wherein a subsequent PRF fraction is obtained from the patient and the subsequent PRF fraction is applied to the capsular contracture by applying the subsequent PRF fraction to the skin by injecting the subsequent PRF fraction adjacent to the capsular contracture and spreading the injected subsequent PRF fraction under the skin by manual manipulation to promote relaxation of the capsular contracture.

8. The method of claim 7, wherein acoustic sound waves or ultrasound waves are applied during the manipulation.

9. The method of claim 5, wherein the PRF fraction is a first PRF fraction and wherein a subsequent PRF fraction is obtained from the patient and the subsequent PRF fraction is applied to the capsular contracture by applying the subsequent PRF fraction to the skin adjacent to said capsular contracture and inducing the transdermal absorption of the subsequent PRF fraction into the skin through pulsed electrical currents, thereby relaxing the capsular contracture.

10. The method of claim 1, wherein the PRF fraction is a first PRF fraction and wherein a subsequent PRF fraction is obtained from the patient, and wherein a subsequent application of PRF is applied to the capsular contracture at least one week after the first PRF fraction is applied to the capsular contracture.

11. The method of claim 1, wherein the PRF fraction is a first PRF fraction and wherein a subsequent PRF fraction is obtained from the patient, and wherein a subsequent application of PRF is applied to the capsular contracture within a 25 day period of the first PRF fraction.

12. The method of claim 1, wherein the capsular contracture exhibits a Baker grade of 3-4 prior to application of the PRF fraction, and inhibition of the capsular contracture by at least one level Baker grade occurs within 30 days of the application.

13. The method of claim 1, wherein the PRF fraction is applied by injection in a first treatment session and transdermally in at least one subsequent the treatment session.

14. The method of claim 1, wherein successive treatment sessions are separated by one week to 25 days.

15. The method of claim 1, wherein myofibroblasts and/or immune cells are obtained from the capsular contracture, and a severity of the capsular contracture is based on data determined from a biopsy of the myofibroblasts and/or immune cells.

16. The method of claim 1, wherein myofibroblasts and/or immune cells are obtained from the capsular contracture, and a treatment volume of the PRF fraction is determined based on data determined from a biopsy of the myofibroblasts and/or immune cells.

17. The method of claim 1, wherein fibrinogen and/or fibrin are obtained from fluid surrounding the capsular contracture, and a severity of the capsular contracture is based on data determined based on characteristics of the fibrinogen and/or fibrin.

18. The method of claim 1, wherein fibrinogen and/or fibrin are obtained from fluid surrounding the capsular contracture, and a treatment volume of the PRF fraction is determined based on data determined from a biopsy of the fibrinogen and/or fibrin.

19. The method of claim 1, wherein an application location for the PRF fraction is determined based on ultrasound data of the capsular contracture.

20. A method for treating capsular contracture of breast implant comprising applying a platelet rich fibrin (PRF) fraction obtained from a patient who exhibits capsular contracture of a breast implant to said capsular contracture, thereby relaxing the capsular contracture.

* * * * *